United States Patent [19]
Jacobsen et al.

[11] Patent Number: 5,860,957
[45] Date of Patent: Jan. 19, 1999

[54] MULTIPATHWAY ELECTRONICALLY-CONTROLLED DRUG DELIVERY SYSTEM

[75] Inventors: Stephen C. Jacobsen; Roland Wyatt; Stephen C. Peterson; Tomasz J. Petelenz, all of Salt Lake City, Utah

[73] Assignee: Sarcos, Inc., Salt Lake County, Utah

[21] Appl. No.: 797,295

[22] Filed: Feb. 7, 1997

[51] Int. Cl.$^6$ .................................................. A61M 65/20
[52] U.S. Cl. ........................ 604/156; 604/30; 604/65; 604/140
[58] Field of Search ................. 604/30, 31, 65–71, 604/118, 131, 140, 151, 153, 156, 246

[56] References Cited

U.S. PATENT DOCUMENTS

| | | |
|---|---|---|
| 3,840,009 | 10/1974 | Michaels et al. . |
| 4,102,332 | 7/1978 | Gessman .............................. 604/67 X |
| 4,141,359 | 2/1979 | Jacobsen et al. . |
| 4,250,878 | 2/1981 | Jacobsen et al. . |
| 4,312,347 | 1/1982 | Morgoon et al. . |
| 4,326,522 | 4/1982 | Guerrero et al. . |
| 4,425,117 | 1/1984 | Hugemann et al. . |
| 4,439,197 | 3/1984 | Honda et al. . |
| 4,457,752 | 7/1984 | Vadasz . |
| 4,564,363 | 1/1986 | Bagnall et al. . |
| 4,968,297 | 11/1990 | Jacobsen et al. . |
| 5,135,479 | 8/1992 | Sibalis et al. .............................. 604/20 |
| 5,196,002 | 3/1993 | Hanover et al. . |
| 5,522,798 | 6/1996 | Johnson et al. ............................ 604/65 |
| 5,527,288 | 6/1996 | Gross et al. ............................ 604/140 |
| 5,582,593 | 12/1996 | Hultman .................................... 604/65 |

*Primary Examiner*—Ronald Stright, Jr.
*Assistant Examiner*—N. Kent Gring
*Attorney, Agent, or Firm*—Thorpe, North & Western, L.L.P.

[57] ABSTRACT

A low-profile multipathway automatic drug delivery system utilizing a battery powered control pad coupled to a disposable drug storage and delivery system and strapped to a patient's limb or torso. A preprogrammed or on-demand drug administration sequence is input to the control pad. When a drug is to be administered, the control pad ignites a high energy density propellant charge in the drug delivery system. Expanding propellant gas exerts pressure on a drug in a second chamber and forces it from the storage reservoir. Depending upon the type of drug delivery system required for the drug being administered, the propellant will either: (i) force a hypodermic needle into a patient's muscle tissue, propel the drug in the storage container into the needle embedded in the patient, and withdraw the needle; (ii) force the drug from the storage container through a jet nozzle where the drug is injected into subcutaneous tissue; (iii) force the drug from the storage container into a patch for passive transdermal delivery; (iv) force the drug into a patch for iontophoretic transdermal diffusion; or (v) force together two drugs stored separately that are unstable when mixed, and then administer them through one of the methods described in steps (i) to (iv).

42 Claims, 6 Drawing Sheets

MULTIPATHWAY ELECTRONICALLY-CONTROLLED DRUG DELIVERY SYSTEM

BACKGROUND OF THE INVENTION

1. Field of the Invention

This invention pertains to a drug delivery system. More specifically, the invention pertains to automatic delivery of a drug or drugs in single or multiple dosages. The invention includes an electronically programmable controller coupled to a low-profile module for attachment to a drug recipient and consisting of a multiple vesicle drug containment system and a plurality of different drug administration methods which are contained therein.

2. State of the Art

Administration of injectable drugs to a patient usually requires a trained and skilled professional to personally prepare the drug, prepare the patient, and administer the drug. If the drug requires injection, a needle must be inserted and removed. Typically, a clinical setting is required for but not limited to this type of drug administration because of the health risks when not using a sterilized environment. Furthermore, monitoring of the patient after drug delivery is often needed to evaluate drug therapy effectiveness or changing patient condition.

Automatically administering drugs without the need for a trained professional has so far met with limited success. To appreciate the dilemma fully, it is necessary to realize that it is not only the personal attention and skills required in administering drugs that make automation difficult to implement, but also the variety of situations in which drugs are administered. A further complication is that the great variety of drugs require different administration techniques.

For example, when a person requires regular insulin injections, that person is taught how to administer injections themselves. If the patient is young, other non-medical personnel are often taught how to administer drugs which severely hinders personal freedom of the drug administrator and the drug recipient. The situation is complicated in an emergency such as when a person goes into shock and is unable to personally inject the medication.

However, it is not only emergencies where automatic administration of drugs can be of benefit. For example, people who must work in confining conditions such as astronauts in space suits, pilots in combat aircraft, or soldiers in combat gear could also benefit from such a drug delivery system. In these situations, the cramped environment prohibits the manipulations necessary to administer a drug by self-administration by conventional means, thus creating a need for the present invention. Similarly, infantry soldiers fighting in the modern combat theater face deadly biological, chemical and nuclear threats that will almost certainly preclude advance drug therapy/prophylaxis of more than a few minutes in advance of critical need due to performance impairing side effects.

It should be apparent from the situations described that there are both military and civilian applications for an automatic drug delivery system capable of administering drugs which require a variety of delivery methods. The prior art solutions are limited in application and typically involve a single delivery method.

One example of a prolonged release drug delivery system that has recently become available is a transdermal patch that delivers a regulated dose of nicotine once it is attached to a smoker's skin. In a lipophilic form, the nicotine is absorbed through the skin, thereby alleviating the cravings for nicotine which is normally obtained through smoking. Unfortunately, very few drugs can be administered transdermally. Furthermore, even those that can be delivered transdermally are not necessarily conveniently administered when needed. There is a need for a drug delivery system that can handle a variety of delivery methods. There is also a need for the system to be automatic once a need for a drug is identified, thereby decreasing the possibility of human error in dosage, timing and delivery, especially under stressful conditions.

As the above situations illustrate, it would be an advantage over the prior art to provide an easily portable, automatic, electronically programmed and controlled multipathway drug delivery system that can be modified for the specific situation in which it will be used. It would be a further advantage if the system could be modified to include such things as programming to provide regular periodic injections, to thereby eliminate the chances of human error. The advantageous system would include different drugs and delivery modalities packaged in one device to provide alternative medical treatments if the drug therapy requirements change. It would also be an advantage over the prior art if a plurality of drugs requiring different delivery methods could all be administered from the same device. The device should be low-profile so that it can be strapped to a person ahead of time before entering an environment where medical attention by conventional means are difficult or impractical for such as reasons as urgency or space constraints. Therefore, ideally the system would be small, light weight, rugged, inexpensive and disposable.

OBJECTS AND SUMMARY OF THE INVENTION

It is an object of the present invention to provide an electronically controlled multi-versicle drug delivery system.

It is also an object of the present invention to provide a programmable electronic drug delivery system controller that provides automatic drug administration without the need for trained assistance.

It is another object to provide a drug delivery system that has a low-profile housing for fitting closely and unobtrusively to a patient because of environmental constraints, to facilitate attachment to a patient, to improve efficiency of the process, or to provide discrete care.

It is another object to provide a drug delivery system that can store and administer a plurality of doses of a single drug at periodic preprogrammed or on-demand intervals.

It is another object to provide a drug delivery system that can store and administer a plurality of different drugs.

It is another object of the present invention to provide sensors for feedback on patient status, enabling the controller to commence drug delivery if sensors indicate a need.

It is another object of the present invention to provide a drug delivery system that can administer drugs using a plurality of different delivery methods, I.e. Multipath delivery modes, in a single device, including passive transdermal, iontophoretic transdermal, subcutaneous spray injection (commonly referred to as needle-less injection) and hypodermic needle injection.

These and other objects not specifically recited are realized in a specific illustrative embodiment of an electronically programmable control unit for use in connection with a low-profile multipathway drug delivery system. A battery powered control pad is coupled to a drug storage and delivery system strapped to a cleaned portion of a human patient's forearm or leg. A preprogrammed or on-demand drug administration sequence is input to the control pad. When a drug is to be administered, the control panel connected to the drug storage/delivery system causes a high energy density thermochemical propellant in the drug delivery system to be ignited. The propellant gas that is produced creates pressure which ejects the drug formulation from the reservoir container. Depending upon the drug delivery route required for the drug being administered, the propellant will either: (i) force a hypodermic needle into the subcutaneous space or into a patient's muscle tissue, inject the drug from the storage container through the needle embedded in the patient, and withdraw the needle; (ii) force the drug from the storage container through a jet nozzle that injects the drug the into subcutaneous space or intramuscularly; (iii) force the drug from the storage container onto a patch in contact with the skin for passive transdermal delivery; (iv) force the drug onto a patch in contact with the skin for iontophoretic transdermal delivery; or (v) force at least two perishable drugs, stored separately, to be mixed, and then administers through one of the methods described in steps (i) to (iv). Included in the methods (I) through (iv) is the provision for reconstitution of a solid drug with a suitable liquid vehicle to form a solution that can be administered by methods (I) to (iv), thereby realizing benefits of solid-state drug stability.

The drug storage and delivery device consists of a plurality of disposable drug storage containers or reservoirs that may contain the same or different drugs, depending upon the particular application of the delivery system, as well as a dispensing module(s). The drug storage containers are arranged so that they can advantageously be disposed of as a unit.

Alternatively, the drug storage containers can individually be removed from the drug storage device for replacement after use or if another drug and its drug delivery system needs to be installed in its place. The individual drug storage containers are interfaced with the appropriate delivery modality (i,e, (i) through (iv) above).

The drug delivery systems all share a common interface to the drug storage unit so that the same electronic signal can trigger or activate any of the storage containers to delivery the drug stored inside. This common interface greatly simplifies the unit in which the drug storage containers are held.

The delivery system advantageously enables different delivery rates of a same drug, depending upon the requirements of the situation. For example, invasive delivery might be preferred when rapid reaction of the patient with the drug is desired. Alternatively, the drug can be delivered non-invasively if slower delivery is desired.

The volume of the drug containers in the drug delivery unit provide precise control of the dose which is applied, and the electronic control pad enables continuous or intermittent drug delivery, as desired. Each individual storage compartment contains a propellant charge, a propellant igniter, a drug reservoir, and an ejection port interface.

The drug delivery mode and pattern can also be controlled by sensors. The sensors provide input to a processing unit that evaluates a patient's condition, then automatically administers the necessary drug(s) in the proper dose.

Also disclosed is a method for automatic, preprogrammed delivery of drugs to a patient, which includes the steps of (i) providing a multipathway electronically-controlled drug delivery system, (ii) attaching the drug storage and delivery module to a patient's torso, forearm or leg, and (iii) programming the control pad to administer the desired drug or drugs in continuous or pulsatile fashion.

DESCRIPTION OF THE DRAWINGS

The above and other objects, features, advantages and alternative aspects of the invention will become apparent from a consideration of the following detailed description presented in connection with the accompanying drawings in which.

DETAILED DESCRIPTION OF THE INVENTION

There are a variety of civilian and military situations which would benefit from an automatic drug delivery system. The system of the present invention can provide 1) multiple doses of a single drug, 2) multiple doses of multiple drugs, 3) drug delivery on demand, and 4) drug delivery over a selectable period of time. These drug delivery options are especially useful when the patient does not possess the skill, time or is otherwise physically challenged so as to prevent administration of a drug or drugs. Likewise, it is also desirable to administer or have available a variety of different drugs within the same drug storage and delivery device. This ability would allow drugs, which require different methods of administration to a patient such as intramuscular (IM) hypodermic injections, subcutaneous jet injections, transdermal iontophoretic drug delivery and passive transdermal drug delivery, to all be easily administered by a single device without the aid of a trained professional, with or without participation of a user (e.g. unconscious patient).

The invention also relates to drug delivery system that can administer drugs as indicated by a combination of patient sensors routed to a microprocessor that evaluates and determines the drug therapy needs of a patient. The delivery system can be programmed to deliver drugs under a predefined regimen such as a large initial bolus followed by smaller therapeutic doses, optionally regulated by sensor feedback, or to administer single doses of different drugs depending on the changing condition of the patient.

Figure 1:
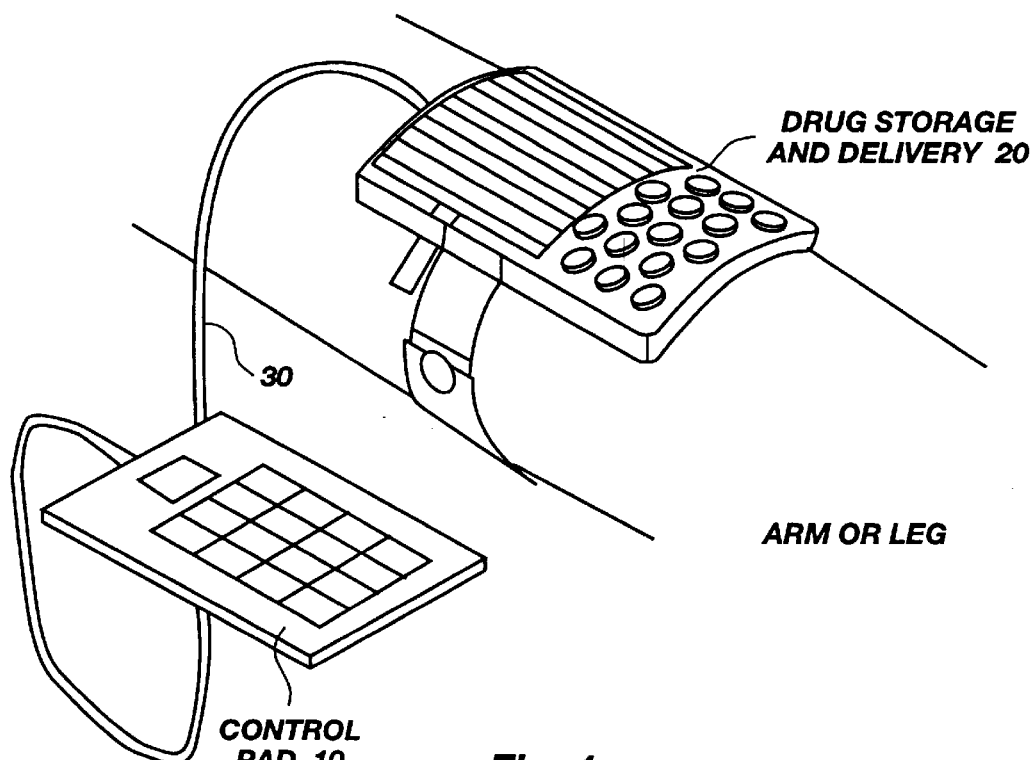
FIG. 1 is a perspective view of all components of a preferred embodiment of a multipathway drug delivery system made in accordance with the specifications of the present invention.

The preferred embodiment of the present invention is illustrated in FIG. 1. The two devices to be described are presented as separate units which communicate via a communication path. However, it is helpful to understand that the present invention can be embodied in a single device. However, because of the advantages of breaking the invention into components, as will be explained, the preferred embodiment as presented hereinafter takes this approach.

FIG. 1 illustrates the components in the preferred embodiment of the present invention in a perspective view. The preferred embodiment of the drug delivery system is comprised of two devices, a control pad 10 and a drug storage and delivery patch or module 20. The module 20 is designed to fit snugly around the contours of a patient's limb or body member, thereby enabling the various drug delivery systems to accurately deliver the drugs when required. The control pad 10 is coupled to the module 20 by any appropriate length of communicating cable 30. An appropriate length os cable 30 enables the control pad 10 to be stored conveniently for access.

The control pad 10 is programmable to thereby select a time of drug delivery, a specific drug which is to be delivered, and the quantity of the desired drug. Selecting a time for drug delivery includes the option of selecting a specific date, a day of the week, or even daily delivery if the drug is to be administered often. A drug can also be delivered more than once on the same day by using a 24 hour clock instead of AM and PM designations to prevent unintended drug delivery errors.

A drug is specifically selected because the drug storage and delivery module 20 is capable of reading a label on a drug storage container as it is inserted, as will be explained. This provides the advantage of being able to select a drug for delivery by name, instead of just by drug storage container position within the module, thereby decreasing the possibility of errors.

Regarding the control pad 10 itself, it has the advantage of being reusable by reconnecting it to another disposable drug storage and delivery module 20 when the drugs stored in the a module are exhausted.

FIG. 1 shows the system as it is typically used in the preferred embodiment of the present invention. A person (hereinafter referred to as a patient) has the torso, forearm or leg cleaned before the module 20 is strapped to it to provide a sterile surface for the drug delivery systems, and to provide a surface which will bond well with the module 20 to prevent movement. The module 20 has a soft and dry sponge-like material underneath (not shown) that lies between the module 20 and the skin, is sterile, and provides double-sided adhesion to prevent module 20 movement. In this embodiment, when the drug storage and delivery module 20 is in storage before use, a foil wrapper protects the sponge from contamination. When the module 20 is applied, the foil is first removed before the module is strapped to the patient. The foil thus also maintains the adhesive surface ready to apply and readily adhere without having to use other bandaging material to secure it to the patient.

The sponge is preferably impregnated with an antiseptic solution. When pressed against the patient, the solution helps prevent infection at an injection site. This is especially helpful when the module 20 will remain on the patient for an extended period of time before or after drug delivery. The sponge-like material also functions as a cushion to prevent irritation of the patient's skin from prolonged wear of the module 20 over an injection site. The sponge will also absorb a small amount of blood that may appear at an injection site upon withdrawal of a needle.

The control pad 10 and drug storage and delivery module 20 are coupled by a wire cable 30 that can be unplugged from either device. The control pad 10 may be mounted on an article of clothing such as a flight suit, space suit or belt loop for convenient access by the wearer. If the cable 30 is sufficiently long, the control pad 10 can be stowed away for protection if ready access is not required.

The nature of the disposable drug storage and delivery module 20 provides the advantages of both non-invasive transdermal and injectable drug delivery systems in a modular unit which can be customized for specific applications and/or individual patients either for single-use (i.e. mission specific), or chronic (multiple injection) therapy applications. The device has both military and civilian medical applications when a person requires a single dose of medication or a combination of several drugs either self-administered or administered by persons with minimal medical training. Civilian applications include self-administration of medications, such as injections of insulin in diabetic patients, epinephrine for anaphylactic shock, narcotic analgesics for treatment of severe pain, or sumatriptan for migraines.

The military has a need for a specialized, user-controlled drug delivery system for rapid administration of medications under field conditions, where manual injections with a syringe are either impractical or require excessive attention or training. Examples of such military applications include delivery of antidotes to chemical warfare agents (anticholinergic drugs such as atropine and 2-PAM), anti-seizure medications, narcotic analgesics and stimulants. Drug administration in such cases must be rapid, simple and reliable, and must minimize impact of human error on selection and administration of drug doses under high stress, life-threatening conditions.

In another embodiment, this system becomes fully automatic through inclusion of sensors that would evaluate a patient's condition and then administer the appropriate drug using the specific programmed delivery protocol for the situation. For example, to increase alertness in critical situations, such as a pilot during a mission, sensors would relay fatigue-indicating information to a controller that would then administer a stimulant according to a predetermined schedule, e.g. initially as a bolus and then tapering off to a maintenance delivery such as by a series of injections or a combination of injections and transdermal delivery. Continual monitoring would ensure that the pilot's alertness would be maintained with the minimal required drug dose. Other conditions such as nausea, pain and injury, or initiation of chemical, biological or nuclear warfare could also be sensed and the correct medication administered. Because the system can be assembled with different drug combinations, it will be mission specific, thus providing optimum medication consistent with mission requirements. It is also envisioned that the delivery portion of the system will be coupled with sensor feedback, allowing remote monitoring of an individual's physiologic status and corresponding adjustment of drug dose, or selection of different medications.

Figure 2:
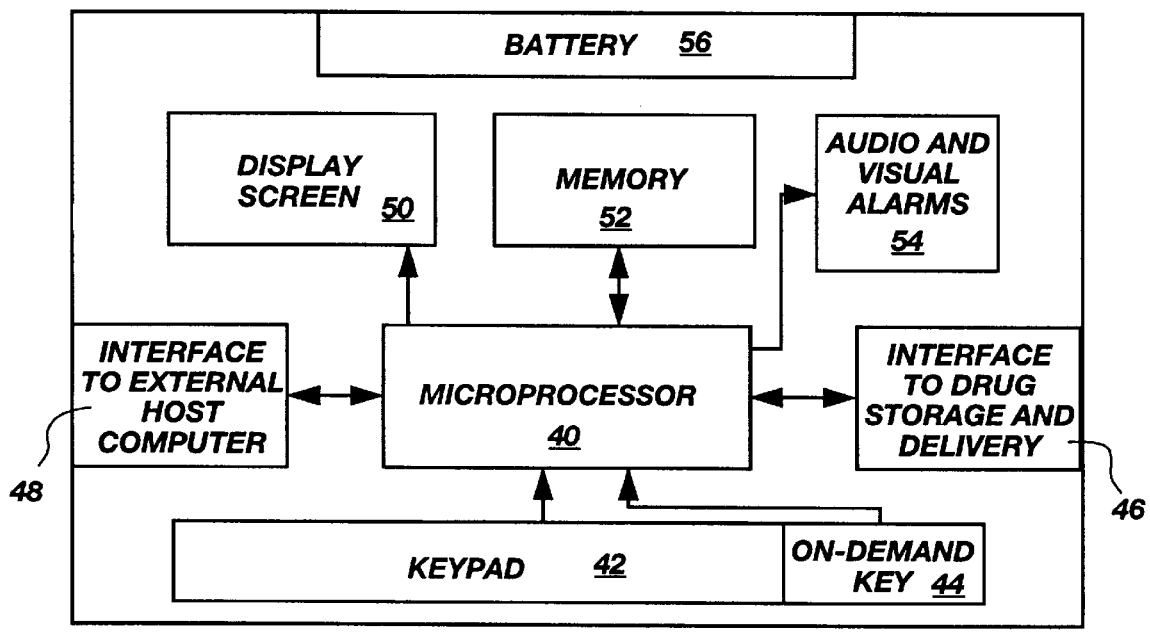
FIG. 2 is a block diagram of the electronic control pad device of the invention illustrated in FIG. 1.

FIG. 2 is a block diagram of the components of the programmable electronic control pad 10 in a preferred embodiment. The control pad 10 will use a low power consuming microprocessor for executing the drug delivery system functions. The microprocessor 40 receives information from a keypad 42, a specialized on-demand key 44, and from two external interfaces. One interface 46 communicates with the drug storage and delivery module 20. A second interface 48 is for communication with an external host computer. Pre-programmed instructions may be received, and stored drug delivery data downloaded via the interface 48. A display screen 50 can display all desired information stored in memory 52. Finally, an audio/visual alarm system 54 alerts a wearer of anomalies or system failures that require attention. It is envisioned that the control pad 10 will be powered by one or two AAA or AA size batteries 56.

The control pad 10 will (i) regulate timing of drug dosing events, (ii) automatically initiate the delivery of drugs, (iii) record the number and completion status of dose dispensing events, (iv) monitor functions of all system components, (v) provide for manual override actuation for on-demand delivery of a selected drug dose, (vi) control visual and audio alarms triggered by results of monitored functions, (vii) display recorded information and system status, (viii) couple to an external host computer to download control pad memory, and (ix) implement power management to prolong battery life.

What may not be obvious from the description is that the control pad display 50 will allow the patient to view drug selection, dosage and timing of preprogrammed events. This can be useful to the patient if the therapy needs to be modified. Furthermore, the external host interface 48 will allow information storage to and retrieval from a computer through a standard "wireless" infra-red RS-232 interface. For example, preprogrammed drug delivery schedules might be fed to the control pad memory 52. More typically, the interface 48 will allow transfer of stored data such as user identification, drug identification, dose and usage information. It is envisioned that the wireless link 48 will eventually enable remote monitoring of a patient's physiological status when the system is equipped with sensors. In addition, the control pad 10 will also run preprogrammed self-diagnostic routines that will alert a user of failure through audio and visual 54 means so that corrective procedures may be implemented to repair the problem.

Another aspect of the control pad 10 is the feature of security protocols. It is sometimes desirable to program a drug delivery schedule and prevent inadvertent or deliberate tampering with the schedule, drug dose or type of drug to be delivered. A security lock-out code can prevent unauthorized tampering. This security feature can also prevent erasure or modification of the drug delivery history which is recorded by the control pad 10 as the drugs are delivered.

The control pad 10 also utilizes power management circuitry to minimize power consumption. This might include powering down certain sections of circuitry such as an interface or other sporadically used feature. In addition, a sleep mode, LCD display 50, and non-volatile RAM 52 will all minimize the drain on battery 56 resources. For example, flash memory might be used to prevent memory loss of drug delivery history or drug delivery schedules even if batteries are removed. One aspect of the invention is the inclusion of a timing circuit having minimal power consumption. Power is increased to the unit on demand or when a scheduled event is to occur.

Control pad 10 design may be customized to a particular application. For example, a control pad 10 for delivery of daily doses of insulin to diabetic patients will have a manual actuation button 44, and will maintain a record of all delivered doses in memory 52. The control pad 10 for automatic delivery based on time or sensor input will be programmable with both timed and sensor triggered actuation, and will have a memory capability to enable storage of data obtained during the interval of use. A different control pad 10 or one with a different scheduling database or history recording capability for delivery of a narcotic will store information on time, frequency and total delivered dose of a drug. This information will be available for subsequent retrieval by a host computer.

A drug encoding scheme is also envisioned such that drug storage reservoirs would have identification bands around the reservoir that could be sensed by circuitry in the delivery module 30 when the drug storage container is placed into a slot in the drug storage and delivery module 20. This information would then be sent through the wire cable 30 to the control pad 10 to enable tracking of drugs. Therefore, even drug container insertion and removal would also be recorded even if no drug is delivered.

One possible coding scheme for drug identification on the drug storage container could be, for example, the use of unique bands and combinations of bands. If four bands were used, a combination of 24, or 16 different drugs could be tracked just by varying the sequence of bands.

In a preferred embodiment, the control pad 10 will be manufactured using surface mount technology components. Later, the electronics will be integrated and a custom ASIC chip will be manufactured.

Figure 3:
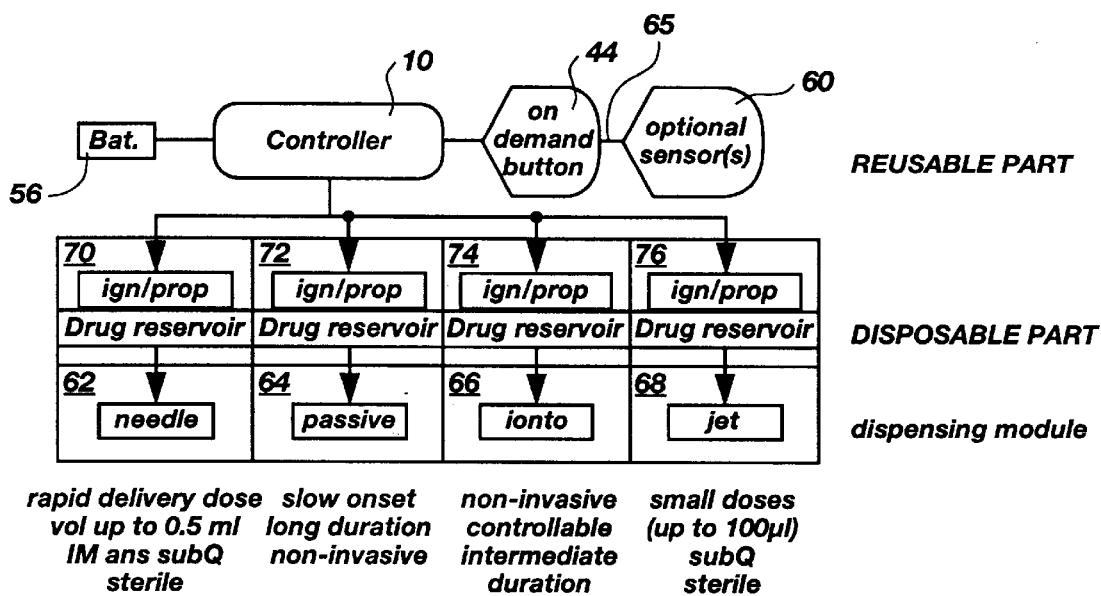
FIG. 3 is a block diagram of the multipathway drug delivery system of FIG. 1.

FIG. 3 is a block diagram of the components of the present invention in a preferred embodiment, and introduces elements not shown in FIG. 1. The control pad 10 is shown to be powered by a battery 56. The battery 56 provides power to both the control pad 10 and the drug storage and delivery module 20 through the wire cable 30. An advantage of providing the battery in the control is that the rug storage and delivery module 20 can be smaller.

It is envisioned that it will be possible to program a dosing event to occur at a specific time (e.g. 10:15 a.m.), an amount of time from when a timer is initiated (e.g. 4 hours 15 minutes after completing programming), or immediately upon demand. Because multiple doses of the same drug, or a variety of different drugs can be administered from the same module 20, multiple drug delivery times can be programmed and stored in control pad memory 56.

Another aspect of the invention is additional input to the control pad 10. In an alternative embodiment, a sensor or plurality of sensors 60 are attached to the patient. The sensor or sensors 60 would be coupled by a second wire cable 65 to the control pad 10. The sensors 60 provide the necessary information for a control pad microprocessor 40 to evaluate a patient's condition as per preprogrammed patient status parameters. This evaluation when compared to the status parameters can trigger the control pad 10 to automatically deliver drugs to the patient, without intervention.

While all embodiments above teach the concept of a hardwired communication path between the control pad 10 and the drug storage and delivery module 20, it should be understood that wireless communications such as radio frequency signals are clearly within the scope of the present invention as a replacement for the wire cables.

The control pad 10 is shown coupled to the drug storage and delivery module 20. The module 20 is shown with four separate delivery systems to illustrate those that are embodied within the present invention. Despite only four distinct delivery systems being shown, this is illustrative only, and the present embodiment anticipates having one delivery system up to a plurality of each different delivery system in the same module 20.

The module 20 is a series of drug delivery modules, each type of which is indicated generally at 62, 64, 66, 68. Each drug delivery module is integrally coupled to respective drug storage reservoirs 70, 72, 74, 76. At the appropriate time, the control pad 10 sends a signal to a propellant igniter circuit in a drug delivery module. In the preferred embodiment of the present invention, the propellant igniter circuit is a solid state small-chip resistor that causes propellant in a chamber of the delivery module to ignite. The resulting propellant gas will cause one of two things to happen. Depending upon the type of delivery module being used, the propellant will either (i) inject a needle into the patient and deliver the drugs from the drug reservoir, (ii) deliver the drugs from the reservoir into a transdermal patch, or (iii) provide needle-less injection. Of course, if a needle is injected, it is automatically removed after drug delivery as part of the injection and extraction process.

Figure 4:
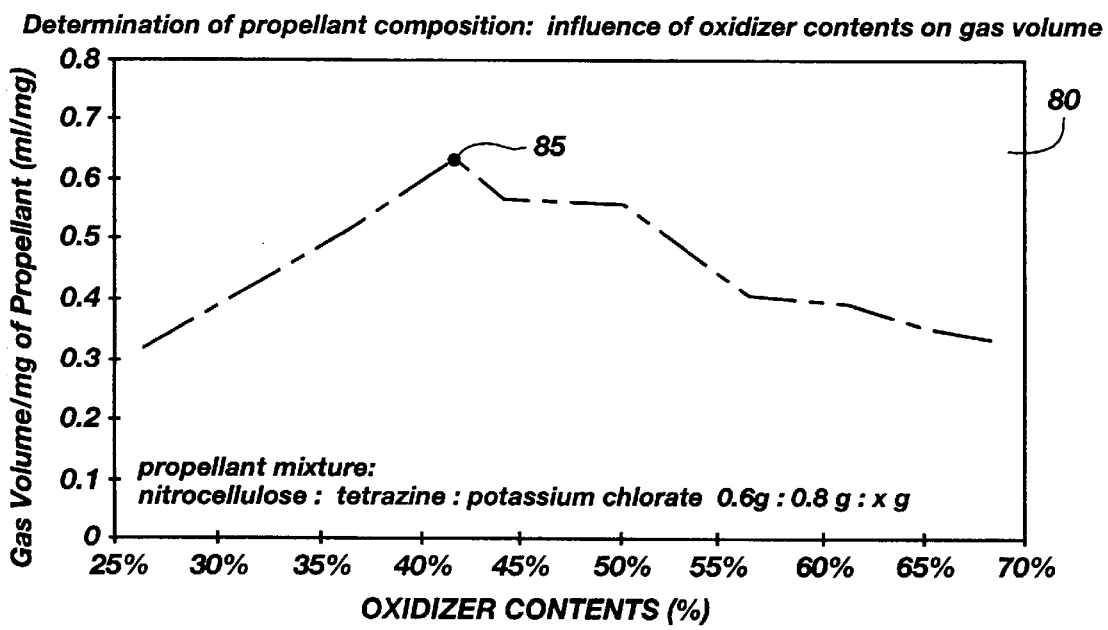
FIG. 4 is a graphical representation of the relationship between gas volume per milligram of propellant and the percentage of oxidizer in the propellant mixture.

FIG. 4 is a graph 80 showing the relationship between the volume of propellant gas created per mg of propellant mixture, versus the percentage of oxidizer in the propellant mixture. As will be shown in greater detail later, a propellant charge is ignited to produce a volume of gas that activates a mechanism or is an actuating force for propelling drugs from storage reservoirs in the various delivery systems. The graph 80 was constructed from test ignitions of propellants to determine the optimal mixture of propellant mixture ingredients for maximum driving force for the delivery systems. Typically, maximum driving force is achieved by creating the largest volume of propellant gas. The point on the graph marked 85 shows the maximum propellant gas volume achieved in experimental propellant ignitions for a given amount of propellant ingredients. This point 85 also corresponds to a percentage of oxidizer in the propellant mixture. The propellant chosen for the preferred embodiment is a tetrazene-nitrocellulose-potassium chlorate mixture. In delivery systems requiring needle injection, the propellant was found to generate sufficient gas volume at sufficient pressure to insert a needle into the patient's tissue, inject a volume of the drug, and then extract the needle as will be further disclosed in FIGS. 8A–D. Some of the important information shown by the graph is that above an oxidizer content of 42%, propellant gas volume per mg of propellant drops off due to the mass contribution of unused oxidizer.

Figure 5:
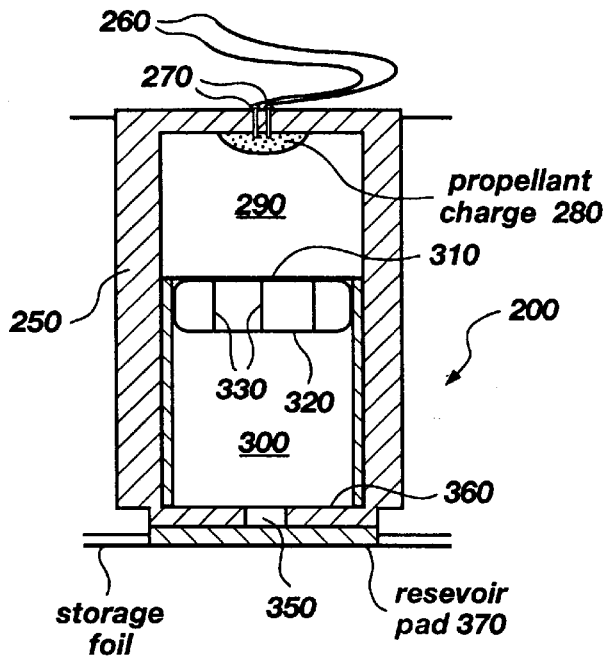
FIG. 5 is a plan view of a transdermal diffusion (passive) device made in accordance with the present invention of FIG. 1.

FIG. 5 is a profile view of a transdermal diffusion drug delivery device 200 as embodied in the present application. The device 200 consists of an outer pod casing 250. The shape of the pod exterior is generally cylindrical. Coupled to the casing 250 at a top end are igniter wires 260 that are connected to probes 270. The probes 270 extend from the outside of the casing 250 where they are attached to the igniter wires 260, through the pod casing 250 to the pod interior. Formed so as to be in physical contact with the probes 270 in the interior of the pod is a propellant charge 280. The charge 280 forms a blister over the probes 270. The pod interior consists in the preferred embodiment of two chambers 290 and 300. The propellant charge 280 is located in the first chamber 290.

The chambers 290 and 300 are separated by a foil barrier 310. The foil 310 rests upon a piston 320 in the second chamber 300, generally dividing the interior into two generally equal halves. The size of the chambers can be modified by changing placement of the foil and piston. The second chamber 300 is a reservoir for the drug being stored in the pod 200. In this preferred embodiment, the piston has grooves 330 which are in sliding engagement with a corresponding grooved path 340 in the wall of the second chamber 300. The grooves 330 ensure that the piston 320 will slide smoothly and evenly down into the second chamber 300 when pressure is applied from the propellant gas expanding in the first chamber 290. To ensure even movement of all sides of the piston 320 down into the drug storage chamber 300, the piston is generally of sufficient thickness and width that it is difficult to cause the piston to move down in any way other than in a smooth and even movement.

At the bottom of the pod casing is an aperture 350 that extends from the pod exterior into the bottom of second chamber 300 and opposite the piston 320. The aperture 350 enables the contents of the second chamber to flow out when compressed by the piston 320. Preventing premature drug delivery is a second foil barrier 360 that lines the bottom of the second chamber 300 and covers the aperture 350.

The procedure for delivering the drug stored in the second chamber 300 to the patient begins when the control pad 10 sends electric current through the igniter wiring 260. The wiring 260 is connected to the probes 270 that deliver the current to the propellant charge 280 surrounding the portion of the probes 270 extending into the first chamber 290. The current traveling through the probes 270 ignites the propellant charge 280, creating a quickly expanding gas confined within the first chamber 290. The gas produces pressure within the first chamber 290 which exerts pressure on the foil barrier 310 which separates the chambers 290 and 300, causing the foil 310 to burst. The gas pressure then forces the piston 320 to compress the contents of the second chamber 300, forcing the drug within the chamber to break the second foil barrier 360 covering the aperture 350, and to be forced out the aperture. The drug flows out of the chamber 300 and, in this particular drug delivery system, fills a pad 370 directly beneath the pod aperture 350. The drug is constrained by the surrounding pad 370, and is absorbed through the patient's skin. The pad 370 can also be a rate controlling membrane which controls the absorption rate of the drug once it is ejected from the chamber 300.

Figure 6:
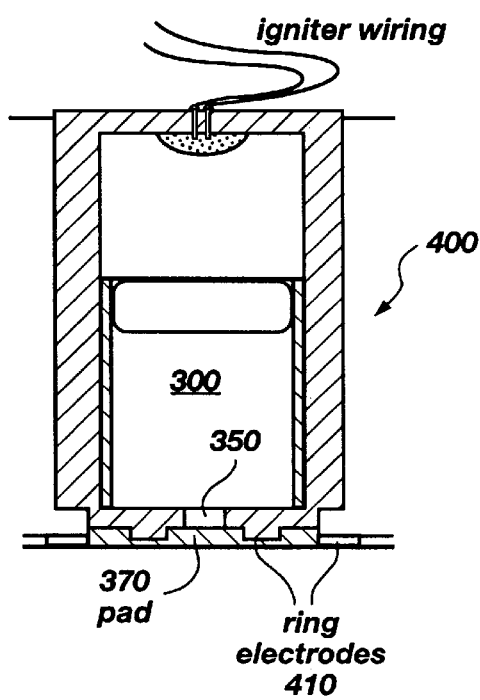
FIG. 6 is a plan view of an iontophoresis delivery device made in accordance with the present invention of FIG. 1.

FIG. 6 is a plan view of an alternative drug delivery system, the iontophoresis delivery device 400 which is similar in structure to the transdermal diffusion device 200. Specifically, both devices 200 and 400 have generally cylindrical exteriors. The structural differences are confined to a series of ring electrodes 410 spaced around the pod aperture 350 from which the drug flows. These ring electrodes 410 are attached to a controlled-current source, and supply a weak electric current to the drug and the patient's skin, allowing for a faster but controlled drug absorption through the skin. Approximately 0.5 ml of drug solution will be contained in the delivery pod chamber 300, separate from the delivery electrodes. This arrangement assures stability of both the drug and the iontophoretic electrodes.

The procedure to deliver the drug from within the second chamber 300 is precisely the same as in the transdermal delivery procedure, with the addition of current being supplied by the control pad 10 through the electrodes 410 to the drug and to the patient's skin immediately subsequent to the drug delivery to the pad 370. Only one electrode delivers current, while the second acts as a return path for the current. It is not important which electrode is doing either function. However, in order to increase the useful lifetime of the electrodes 410, polarity of both electrodes is switched periodically.

The pH balance within the application area is controlled using two Ag/AgCl electrodes 410 with a drug in hydrochloride form, with current not exceeding 0.1 mA/cm$^2$. For this reason, drug selection for iontophoresis is usually limited to lipophilic compounds of moderate-to-high potency, with good aqueous solubility, preferably available as hydrochloride salts. However, if a hydrochloride salt of a preferred drug is not available, ion exchange resins will be used to control the pH and efficiency of iontophoretic delivery.

Figure 7:
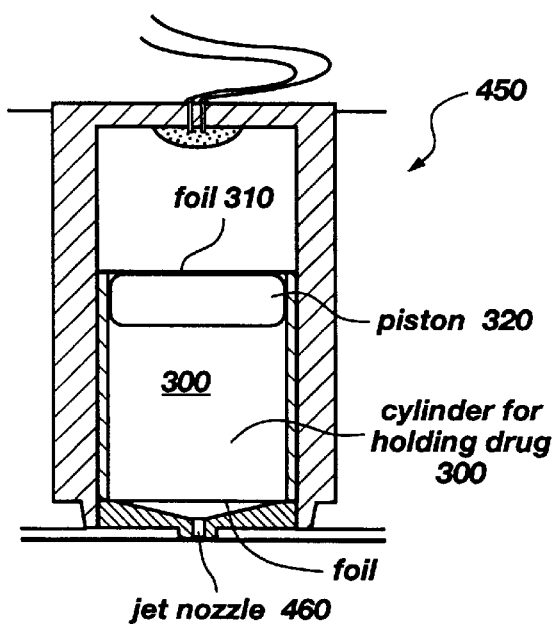
FIG. 7 is a plan view of a fluid jet delivery device made in accordance with the present invention of FIG. 1.

FIG. 7 is a plan view of a fluid jet drug delivery device 450, also similar in structure to the transdermal diffusion device 200. The structural differences appear around the aperture 460 from the second chamber 300. Specifically, the aperture 460 is substantially smaller than the aperture 350 in the transdermal 200 and iontophoresis 400 systems. The aperture 460 forms a jet nozzle that, unlike the other apertures 350, is in direct contact with the patient's skin. Contact is necessary to facilitate the delivery of the drug directly into the patient's tissue. The drugs is injected through the skin and is quickly absorbed.

The drug delivery procedure operates in the same manner as the other systems, ending with the piston 320 forcing the drug in the second chamber 300 through the jet nozzle 460 directly through the patient's skin. By creating a sufficiently large pressure and using a small nozzle, the drug is inserted into subcutaneous skin layers without a needle, as will be understood by those skilled in the art.

Use of the fluid jet system 450 necessarily requires drugs that can be effectively delivered in small dosage volumes. About 3 MPa of pressure is required to penetrate the skin when the drug is delivered through a 100 micrometer nozzle. Propellant charges 280 can produce several hundred KPa of pressure (several atmospheres) using only a few milligrams of propellant. Results have shown that for a propellant piston area of about 1 square centimeter, 0.1 ml of drug could be delivered at the required 3 MPa pressure. As is obvious to those skilled in the art, multiple modules could deliver an aggregate larger quantity of drug as needed, easily overcoming the problem of finite drug storage container size. However, practicality of this drug delivery system 450 approach generally but does not exclusively depend on selection of potent drugs and formulations active at low (in the range of 100 to 200 microliter) injection volumes.

Figure 8A:
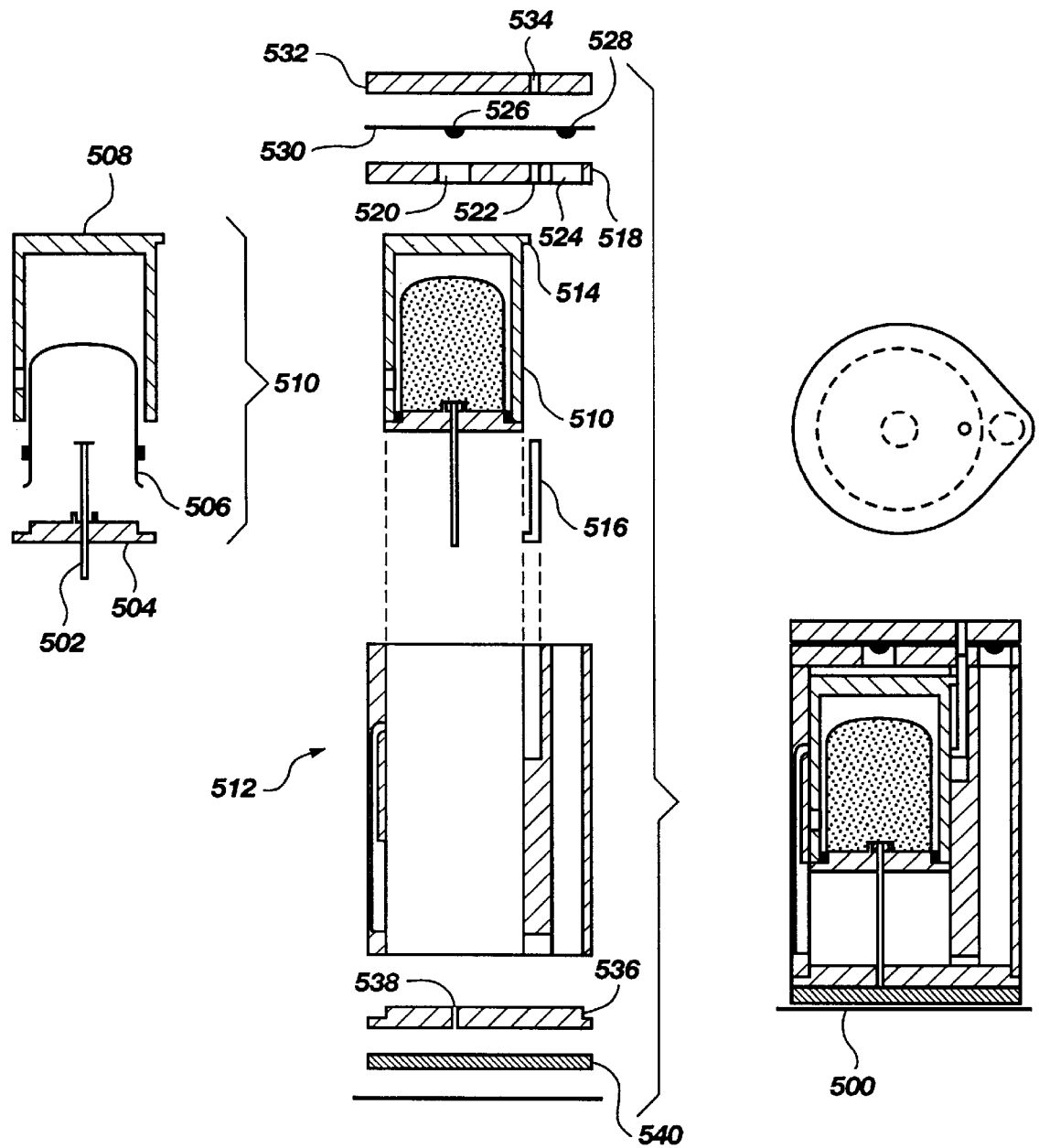
FIG. 8A is a plan view of a hypodermic needle delivery device made in accordance with the present invention of FIG. 1.

FIG. 8A is a plan view of a preferred embodiment of the hypodermic needle drug delivery device 500, which has significant internal structural differences from the three devices already disclosed. The internal structure is necessarily more complicated in design because a needle must not only be injected into the patient, but the drug delivered and the needle subsequently withdrawn. These three processes cannot be activated from the action of a single charge. Consequently, the system is further complicated by the addition of a second charge to complete the three processes.

The components of the drug containment pod are shown as a needle 502, a sealing ring 504, a drug containment pouch 506, and a pod cylinder 508. This unit 510 fits in sliding engagement within a larger pod cylinder 512, which has various passages for pressurized propellant gas to flow. The drug pod 510 slides down into the larger pod 512 so that the top of the drug pod is slightly lower than the top of the larger pod. A lip 514 of the drug pod extends outwardly from the drug pod so as to form a catch to stop the sliding movement of the drug pod. Beneath the lip and resting between the drug pod 510 and the larger pod 512 is a small L-shaped plug 516. The plug is inserted into the large pod before the drug pod, but extends upward past the top of the drug pod before drug delivery as shown.

Above the drug pod 510 is a first cap 518 with three apertures 520, 522, 524. A first aperture 520 forms a space for a propellant charge 526 to be situated directly above the drug pod 510. A smaller second aperture 522 is a small hole that allows expended propellant gas to flow from the large pod 512 after the drug has been delivered. This aperture 522 is initially sealed by the portion of the L-shaped plug 516 that extends upward past the top of the drug pod 510. A third aperture 524 forms a space for a second propellant charge 528. Above the first cap 518 is a second cap 532 with a single aperture 534 that allows expended propellant gas to flow out when the second aperture 522 is not sealed by the L-shaped plug 516.

The propellant charges 526 and 528 are connected to a flex circuit 530. The circuit provides a path for electrical current from the control pad 10 to ignite the charges, just as the ignition wires accomplish this function in other delivery devices.

Below the large pod 512 is a bottom cap 536 that seals the large pod shut. A single aperture 538 extends through the bottom cap which serves as a path for the hypodermic needle 502. Beneath the bottom cap is a needle guard and seal 540. The guard is a protective silicone rubber septum to keep the needle end sterile. The guard will be punctured upon ignition of the first propellant charge 526. The needle guard also prevents the needle from inadvertently sliding out of the large pod 512, inadvertently scratching a patient or being bent should the L-shaped sealing plug 516 be knocked out of the second aperture 522. A final assembled version of the hypodermic needle delivery pod 500 shows the arrangement of components before drug delivery, as well as a view from above the pod.

Figure 8B:
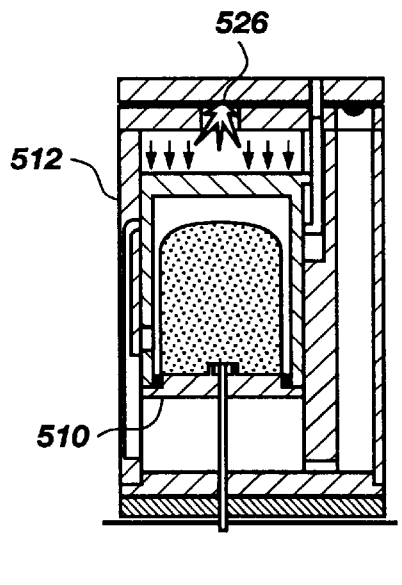
FIGS. 8B, 8C, and 8D are plan views illustrating the action of the hypodermic needle delivery device components of FIG. 8A when activated to deliver a drug.
Figure 8C:
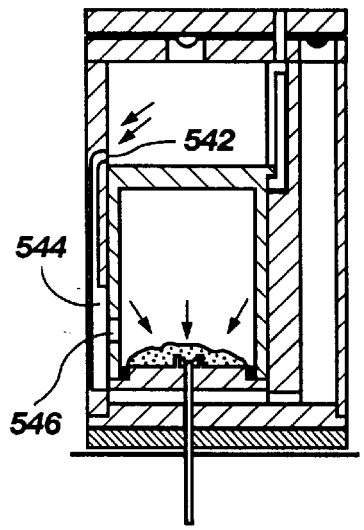
Figure 8D:
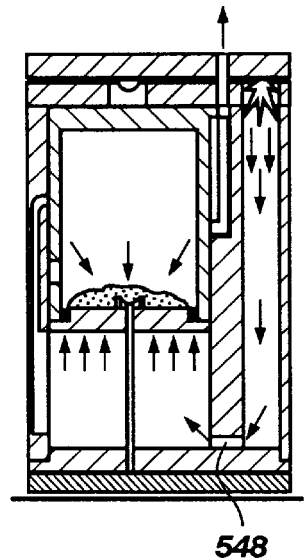

FIGS. 8B, 8C and 8D illustrate the movement of hypodermic needle pod 500 components as the control pad 10 initiates a drug delivery sequence. FIG. 8B shows the first propellant charge 526 is ignited by a signal from the control pad 10 (not shown) which forces the drug pod 510 downward inside the large pod 512. As the drug pod 510 descends, three events occur as illustrated by FIG. 8C: (i) the lip 514 at the top of the drug pod 510 engages the bottom lip of the L-shaped sealing plug 516, pulling the pin down and unsealing the second aperture 522, 524, (ii) the hypodermic needle 502 pierces the needle guard and seal 540 and the skin of a patient to an approximate depth of 5 mm, and (iii) when the drug pod slides down past the opening 542 of a propellant gas flow passageway 544, the expanding gas flows into an aperture 546 in the side of the drug pod 510, collapsing the drug-containment pouch 506 and forcing a drug through the hypodermic needle into the tissue of the patient.

Finally, FIG. 8D shows that after drug delivery the control pad 10 ignites the second propellant charge 528. The expanding gas passes through another gas passageway 548 and forces the drug pod 510 upward, extracting the hypodermic needle 502 from the patient's tissue. The needle cannot slide down out of the large pod 512 because the drug pod 510 is being suspended by the pressure exerted by the gas from the second propellant charge 528. It is envisioned that needle extraction may be accomplished by methods other than a second propellant charge, such as a return spring activated by completion of drug delivery.

Figure 9:
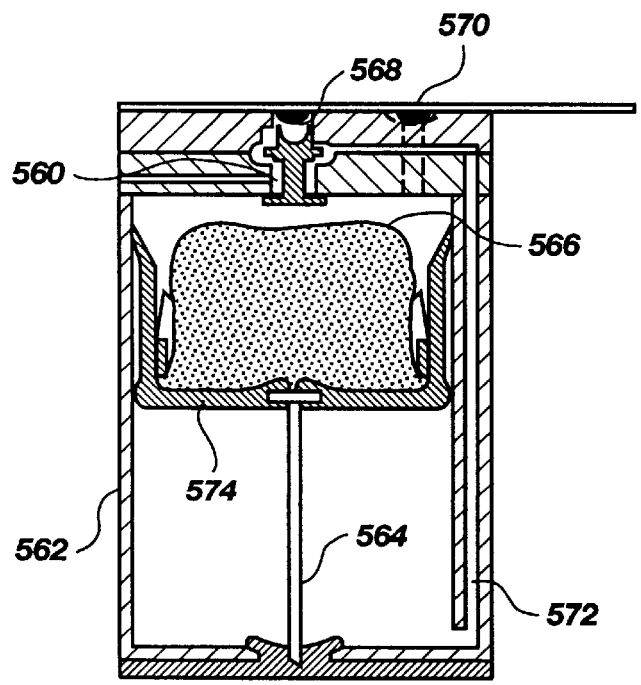
FIG. 9 is a plan view of an alternative embodiment of the hypodermic needle delivery system of FIG. 8A.

FIG. 9 is a plan view of an alternative embodiment of the hypodermic needle drug delivery system. In this embodiment, a miniature rubber stopper-valve 560 is inserted into the upper lid of the cylinder 562. This valve 560 enables two way venting of excessive gas pressure during both needle 564 injection and needle 564 withdrawal. A drug pouch 566 is loose, so it is the pressure of the expanding gas from a propellant charge 568 which first drives the needle 564 down into the patient, and then injects a drug within the pouch 566. Proper selection of needle diameter is required so that frictional resistance of fluid injection is significantly higher than that during needle 564 insertion. After the drug has been injected, a properly timed second propellant charge 570 is ignited. The resulting propellant gases travel down the smaller channel 572 where they push the drug pouch housing 574 upwards, similar to the method of operation of FIGS. 8B, 8C and 8D. This motion of the drug pouch housing 574 pulls the needle 564 from the patient.

Figure 10:
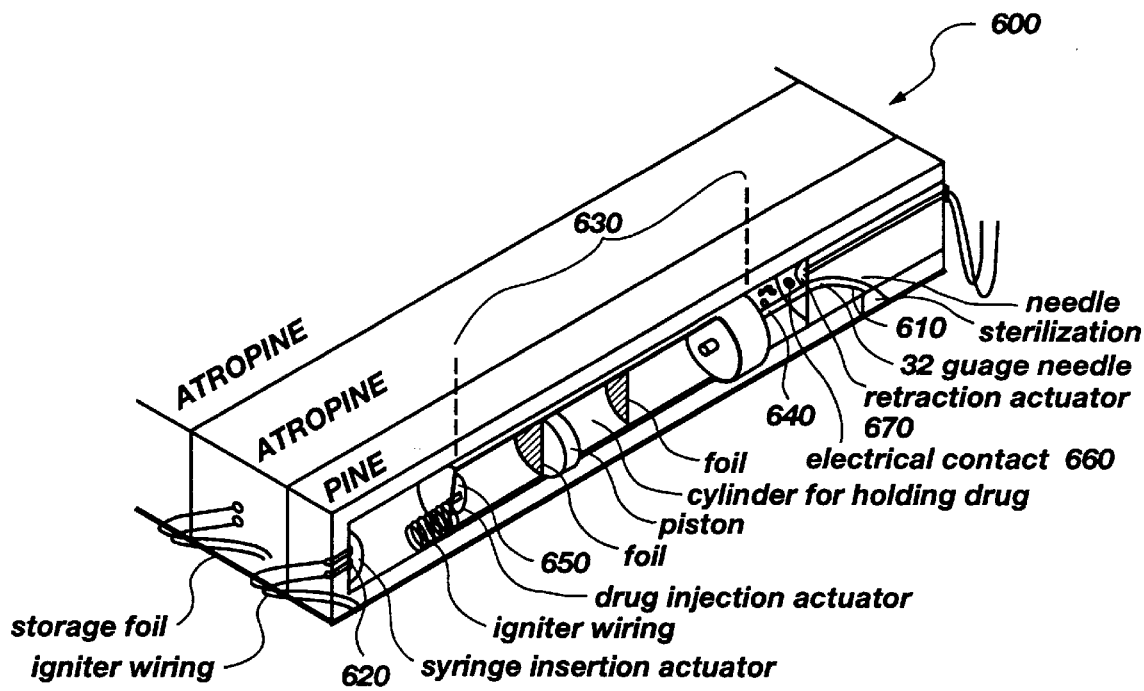
FIG. 10 is a perspective plan view of a low-profile hypodermic needle injection delivery system of FIG. 8A.

FIG. 10 shows a perspective view of a low-profile hypodermic needle injector device 600. This embodiment does not require vertical injection. Instead, to obtain the required needle penetration for IM injection (about 5 mm) and to maintain a low profile package, the needle may need to traverse a 90 degree bend 610. This bending necessitates a small diameter needle (e.g. 32 Ga) and additional "insertion" force to overcome the friction of the needle traveling through the bend 610. This is accomplished by using a propellant charge 620 that is designed to propel a sliding drug delivery pod 630 down a larger tube, and propel a needle 640 protruding from the sliding pod 630 through the 90 degree bend 610. Once the needle 640 is inserted through the bend and into the patient, a second propellant charge 650 is needed to expel the drug through the small bore of the needle, overcoming the Poiseuille pressure drop associated with the fluid flowing through the needle. The sliding delivery pod structural interior is basically similar to the internal pod structure used in the transdermal 200, iontophoretic 400 and fluid jet 450 delivery systems, except that the ejection aperture is a needle.

After the drug is delivered, the needle 640 needs to be withdrawn from the patient. An electrical contact 660 senses when the slidable delivery pod 630 has been forced down the tube. After waiting a specified amount of time after contact during which the drug is delivered, a third propellant charge 670 ignites to create sufficient gas pressure on the slidable pod to move it back into the tube, extracting the needle from the patient. The slidable pod 630 will not have to be anchored because there is no longer any way to create a force sufficient to drive the needle through the 90 degree bend.

Figure 11:
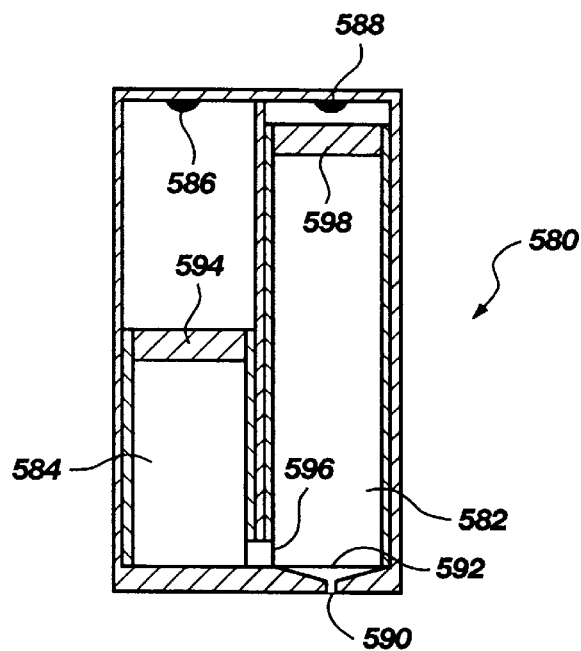
FIG. 11 is a plan view of a drug delivery system that permits two components of unstable drugs to be stored separately until administration to a patient.

FIG. 11 is a profile view of a preferred embodiment for a drug storage and delivery pod 580 that contains two separate drug storage reservoirs. The pod enables delivery of a drug that is a combination of elements that can only be mixed immediately prior to injection because of the nature of the drug. For example, 2-PAM is a drug that is stored dry. The drug is mixed with a liquid solution and then injected. Therefore, the pod must not only enable delivery of the drug, but mixing of pod container contents before delivery. Furthermore, the delivery system must be able to mix two liquids together, as well as one liquid and a solid powder.

A preferred embodiment of a system which can mix two liquids, or a liquid with a solid, is shown in FIG. 11. The first chamber 582 will typically be half full of a part of the drug to be mixed, thereby allowing room for the other part of the drug to enter without exerting pressure on the foil 592. When a first propellant charge 586 is ignited, the drug in a second chamber 584 is forced by a descending plunger 594 through a one-way valve 596. The drugs are then permitted time to mix within the first chamber 582. In an alternative, a mixing means can be provided to more thoroughly mix the drugs, or simply to speed up the mixing process. After mixing, a second propellant charge 588 is ignited causing a second plunger 598 to force the drug from the first chamber 582 and through the jet needle 590.

It should be apparent that other drug delivery methods can be implemented other than the jet nozzle system shown, including those using a hypodermic needle to inject the mixed drug. The example shown in FIG. 11 is only meant to be exemplary of the many ways in which two drugs can be stored separately, mixed rapidly, and injected into the patient.

It is to be understood that the described embodiments of the invention are illustrative only, and that modifications thereof may occur to those skilled in the art. Accordingly, this invention is not to be regarded as limited to the embodiments disclosed, but is to be limited only as defined by the appended claims herein.

What is claimed is:

1. A multipathway automatic and on-demand drug delivery system for multiple administrations at selectable dispensing times of at least one type of drug, said system comprising:

a plurality of drug storage and delivery means wherein each has at least one drug storage reservoir and an actuable drug delivery system which receives a signal causing the drug delivery system to eject the at least one type of drug from the at least one drug storage reservoir, said plurality of drug storage and delivery means comprising:

a plurality of generally hollow dual-chambered delivery pods having an enclosed top face and bottom face, and where the chambers are generally arranged as an upper chamber and a lower chamber;

the upper chamber which functions as a propellant chamber having a ceiling a combustible propellant charge in the propellant chamber which is proximate to the ceiling;

an ignition means for igniting the combustible propellant charge;

a piston located between the propellant chamber and the lower chamber, wherein said piston has generally flat top and bottom faces;

the lower chamber functioning as a drug reservoir chamber situated beneath the piston, having the piston as a ceiling, a puncturable membrane associated with said drug reservoir chamber; and an outlet port beneath the puncturable floor membrane and extending through an aperture in the bottom face of the drug reservoir chamber to enable ejection of the drug therefrom;

a drug storage and delivery module which holds the plurality of drug storage and delivery means in position until ejection of the at least one type of drug therefrom;

a securing means for coupling the drug storage and delivery module to a patient; and a control means which is coupled to the drug storage and delivery module and which transmits the signal causing the drug delivery system to eject the at least one type of drug at the selectable dispensing times.

2. The drug delivery system as defined in claim 1 wherein the control means which communicates bidirectionally with the drug storage and delivery module is coupled therebetween via a hardwired communication link.

3. The drug delivery system as defined in claim 2 wherein the hard-wired communication link is selected from the group of hard-wired communication links consisting of coaxial cable, twisted pair, straight wire, and optical fiber.

4. The drug delivery system as defined in claim 1 wherein the control means which communicates bidirectionally with the drug storage and delivery module is coupled therebetween via a wireless communication link.

5. The drug delivery system as defined in claim 4 wherein the system further comprises a sensor means coupled to the control means for monitoring physiological parameters of the patient and providing them to the control means, and wherein drug therapy is modifiable based upon the physiological parameters from the sensor means.

6. The drug delivery system as defined in claim 4 wherein the control means further comprises:
   a data entry means for programming instructions into control means memory to regulate drug administration;
   a display means for showing programmed instructions, recorded information and system status;
   a processing means for executing programmed instructions;
   a memory means for storing programmed instructions and for recording drug administration data;
   a first interface means for transferring information stored in the memory means to and from an external information host; and
   a second interface means for communicating with the drug storage and delivery module.

7. The drug delivery system as defined in claim 6 wherein the data entry means is a keypad for interfacing with the control means, and which includes an on-demand button for immediate delivery of a desired drug from the drug storage and delivery means.

8. The drug delivery system as defined in claim 6 wherein the control means is battery powered for mobile operation of the system.

9. The drug delivery system as defined in claim 6 wherein the display means further comprises a liquid crystal display (LCD) screen.

10. The drug delivery system as defined in claim 6 wherein the processing means for executing programmed instructions further comprises a programmable processor.

11. The drug delivery system as defined in claim 6 wherein the memory means for storing programmed instructions and for recording drug administration data further comprises non-volatile RAM that will retain memory contents when power to RAM is removed.

12. The drug delivery system as defined in claim 11 wherein the memory means for storing programmed instructions and for recording drug administration data is comprised of flash memory.

13. The drug delivery system as defined in claim 6 wherein the interface means for transferring information stored in the memory means to an external host is comprised of an RS-232 interface.

14. The drug delivery system as defined in claim 1 wherein the drug storage and delivery means are selected from the group of delivery systems consisting of iontophoretic delivery means, transdermal diffusion delivery means, fluid jet delivery means, hypodermic needle delivery means, pre-delivery drug mixing means, and needle delivery means.

15. The drug delivery system as defined in claim 14 wherein the iontophoretic, transdermal diffusion, and fluid jet delivery means further comprise:
   at least two electric leads extending from outside the top face of the pod and through the top face and extending partially into the propellant chamber through the ceiling of said propellant chamber;
   said ignition means for igniting the combustible propellant charge coupled to the at least two electric leads and covered by the combustible propellant charge; and
   an outlet port beneath the puncturable floor membrane and extending through an aperture in the bottom face of the drug reservoir chamber to enable ejection of the drug therefrom.

16. The drug delivery system as defined in claim 15 wherein the drug reservoir chamber is provided in a plurality of different sizes to allow variation in drug dosages which may be delivered by the system.

17. The drug delivery system as defined in claim 1 wherein the drug storage and delivery means is disposable.

18. The drug delivery system as defined in claim 15 wherein the plurality of generally dual-chambered delivery pods further comprise generally cylindrical shapes, wherein the walls of the upper and lower chambers are generally circular, and wherein the piston is a generally circular disk which is slightly smaller in diameter than the drug reservoir chamber to thereby enable the piston to descend into said chamber.

19. The drug delivery system as defined in claim 15, wherein said piston has generally flat top and bottom faces and at least one side edge having a plurality of vertical grooves, and wherein the lower chamber having a vertically grooved wall, said grooves meshing in sliding engagement with the vertical grooves of the piston so as to provide a channel for the piston to follow when the piston descends upon the lower chamber.

20. The drug delivery system as defined in claim 15 wherein the ignition means further comprises a chip resistor which is heated by electrical current provided by one of the at least two electric leads.

21. The drug delivery system as defined in claim 14 wherein the transdermal diffusion device further comprises a reservoir pad whereby a drug in the drug reservoir chamber is forced from said chamber onto skin of a patient when the membrane is punctured from increasing pressure in the drug reservoir chamber when the piston descends on said chamber, and wherein said drug is prevented from flowing off the skin by the reservoir pad which maintains the drug in contact with the skin until absorbed.

22. The drug delivery system as defined in claim 15 wherein the transdermal diffusion device further comprises a reservoir pad whereby a drug in the drug reservoir chamber is forced from said chamber onto a rate controlling membrane which is in contact with skin and which enables gradual absorption of the drug.

23. The drug delivery system as defined in claim 15 wherein the fluid jet delivery device further comprises a narrow aperture whereby the drug in the drug reservoir chamber is forced from said chamber directly into a subcutaneous layer of a patient's skin when the floor membrane is punctured from increasing pressure in the drug reservoir chamber when the piston descends on said chamber.

24. The drug delivery system as defined in claim 15 wherein the iontophoretic delivery device further comprises a reservoir pad and wherein a drug in the drug reservoir chamber is forced from said chamber when the floor membrane is punctured from increasing pressure in the drug reservoir chamber when the piston descends on said chamber, wherein said drug is prevented from flowing off the skin by the reservoir pad, and wherein electrodes from the drug storage and delivery module are in contact with the skin to thereby provide a weak electrical current thereto.

25. A multipathway automatic and on-demand drug delivery system for multiple administrations at selectable dispensing times of at least one type of drug, said system comprising:
   a plurality of drug storage and delivery means wherein each has at least one drug storage reservoir and an actuable drug delivery system which receives a signal causing the drug delivery system to eject the at least one type of drug from the at least one drug storage reservoir, said plurality of drug storage and delivery means comprising:

an inner pod cylinder sealed at both ends and having a rigid cylindrical housing, wherein said inner pod comprises:
(i) a top lid has a lip extending horizontally from the side of said lid, (ii) a first gas entry port in a wall, (iii) a bottom lid from which a needle extends perpendicularly through an aperture, and (iv) a collapsible membrane anchored to the bottom lid and surrounding a needle inlet port that extends into the bottom lid, and wherein a drug is stored within said membrane;

an outer pod cylinder within which the inner pod cylinder fits in sliding engagement, wherein said outer pod comprises:
(i) an uppermost lid with a single gas vent, (ii) a flex circuit with a first and a second propellant charge thereon which is fixed to the bottom of said uppermost lid, (iii) a second lid with said single gas vent, (iv) a first propellant charge aperture positioned so as to encircle the first propellant charge that extends downward through said aperture, (v) a second propellant charge aperture positioned so as to encircle the second propellant charge that extends downward through said aperture, (vi) an L-shaped plug positioned to initially seal the single gas vent and to catch the horizontal lip of the inner pod when the inner pod descends a distance down through the outer pod, (vii) a recessed groove with a ledge on an outer pod inner wall to hold the L-shaped plug and allow vertical movement of the inner pod horizontal lip and the plug until said lip and said plug reach the ledge, (viii) a propellant gas passage through the outer pod inner wall that enables first propellant charge gas to enter, flow through said passage and enter the inner pod through the first gas entry port, (ix) a second bottom lid which seals the outer pod, with an aperture through said lid for the needle, (x) a needle guard that surrounds the injectable end of the needle, and (xi) a second propellant gas passage leading from the second propellant gas charge to flow underneath the inner pod;

a drug storage and delivery module which holds the plurality of drug storage and delivery means in position until ejection of the at least one type of drug therefrom;

a securing means for coupling the drug storage and delivery module to a patient; and a control means which is coupled to the drug storage and delivery module and which transmits the signal causing the drug delivery system to eject the at least one type of drug at the selectable dispensing times.

26. The drug delivery system as defined in claim 25 wherein the needle guard comprises a silicone rubber septum.

27. A multipathway automatic and on-demand drug delivery system for multiple administrations at selectable dispensing times of at least one type of drug, said system comprising:

a plurality of drug storage and delivery means wherein each has at least one drug storage reservoir and an actuable drug delivery system which receives a signal causing the drug delivery system to eject the at least one type of drug from the at least one drug storage reservoir, said plurality of drug storage and delivery means comprising:

at least one straight and hollow cylindrical housing having an exterior and interior back end and front end;

a cylindrical hypodermic needle delivery pod which moves in sliding engagement within the length of the housing, and which is distally disposed from the front end of the housing before actuation;

means for injecting a hypodermic needle, which is coupled to the hypodermic needle delivery pod, through an aperture in the housing and into a patient, comprising:
a first pair of ignition leads coupled to the control means and which extend through the exterior and partially into the interior of the back end of the housing; and
ignition means disposed within and coupled to the two ignition leads in the interior of the housing for igniting a combustible propellant charge, the combustible propellant charge surrounding the ignition means and which will ignite responsive to the signal applied to the first pair of ignition leads, thereby forcing the hypodermic needle delivery pod toward the front end of the housing, and causing the hypodermic needle to penetrate a patient's skin;

means for extracting the hypodermic needle from the patient after drug injection, a drug storage and delivery module which holds the plurality of drug storage and delivery means in position until ejection of the at least one type of drug therefrom;

a securing means for coupling the drug storage and delivery module to a patient; and a control means which is coupled to the drug storage and delivery module and which transmits the signal causing the drug delivery system to eject the at least one type of drug at the selectable dispensing times.

28. The drug delivery system as defined in claim 27 wherein the at least one straight and hollow cylindrical housing is disposed perpendicular to the arcuate angle of the drug storage and delivery module to thereby lie along a length thereof.

29. The drug delivery system as defined in claim 27 wherein the hypodermic needle delivery means is more specifically comprised of an aperture that has an opening which begins parallel to the length of and from within the housing interior at the front end and which forms an arcuate path that exits the housing at a right angle relative to the opening and which is directed out the underside of the drug storage and delivery module.

30. The drug delivery system as defined in claim 29 wherein the hypodermic needle delivery means is more specifically comprised of a hypodermic needle coupled to a drug reservoir within the hypodermic needle delivery pod, and extending from a front end of said pod and lying within the aperture but not extending therefrom.

31. The drug delivery system as defined in claim 30 wherein the means for extracting the hypodermic needle from the patient after drug injection is more specifically comprised of:

an electrical contact disposed at the front end of the housing interior and which generates a second signal when the drug delivery pod has made contact with the front end;

a second pair of ignition leads coupled to the control means and which extend through the exterior and partially into the interior of the front end of the housing;

second ignition means disposed within and coupled to the second pair of ignition leads in the front end of the interior of the housing for igniting a second combustible propellant charge; and the second combustible propellant charge disposed to surround the ignition means and which will ignite responsive to the second signal, thereby forcing the hypodermic needle delivery pod toward the back end of the housing, causing the hypodermic needle to be extracted from the patients.

32. The drug delivery system as defined in claim 27 wherein the at least one straight and hollow cylindrical housing is disposed to extend perpendicularly from a plane of the patient's leg or arm.

33. The drug delivery system as defined in claim 32 wherein the cylindrical hypodermic needle pod more specifically comprises a collapsible drug containment pouch and a hypodermic needle extending therefrom.

34. The drug delivery system as defined in claim 33 wherein the system further comprises:

a first chamber defined as a space bounded by the top of the housing, a generally circular wall and the hypodermic needle delivery pod, said first chamber initially holding a first expanding propellant gas from a first combustible propellant charge;

a second chamber defined as a space bounded by the hypodermic needle delivery pod, and in which the collapsible drug containment pouch is disposed;

a first propellant gas flow passageway from the first chamber to the second chamber which is open for gas flow after the hypodermic needle delivery pod is forced down the length of the housing by the expanding propellant gas in the first chamber;

a third chamber defined as a space bounded by the hypodermic needle delivery pod, a generally circular wall and the bottom of the housing, after the hypodermic needle delivery pod has completely descended in the housing;

a plug which is pulled down with the hypodermic needle delivery pod to expose a second propellant gas passageway from the first chamber to outside of the housing thereby enabling the first expanding propellant gas to escape from the housing when the hypodermic needle delivery pod is forced back to the top of the housing;

a fourth chamber in which a second combustible propellant charge is ignited to create a second expanding propellant gas; and a third propellant gas flow passageway from the fourth chamber to the third chamber which enables the second expanding propellant gas to force the hypodermic needle delivery pod from the bottom of the housing back to the top of the housing.

35. The drug delivery system as defined in claim 34 wherein the means for injecting a hypodermic needle into the patient is more specifically comprised of a first propellant blister formed from a first combustible propellant charge and an electric circuit for igniting the first combustible propellant charge to thereby create the first expanding propellant gas.

36. The drug delivery system as defined in claim 35 wherein the means for extracting the hypodermic needle from the patient after drug injection is more specifically comprised of a second propellant blister formed from a second combustible propellant charge and a second electric circuit for igniting the second combustible propellant charge to thereby create the second expanding propellant gas.

37. The drug delivery system as defined in claim 15 wherein the propellant charge further comprises a tetrazene-nitrocellulose-potassium chlorate and oxidizer mixture.

38. The drug delivery system as defined in claim 1 wherein the sterile pad coupled to the underside of the drug storage and delivery module has an adhesive surface for attachment to the limb.

39. The drug delivery system as defined in claim 1 wherein the drug storage and delivery module is contoured to couple to a patient's arm, leg or torso to provide a reliable contact for drug administration.

40. The drug delivery system as defined in claim 39 wherein the drug storage and delivery module has a low profile to minimize interference with a patient's activities when being worn.

41. The drug delivery system as defined in claim 1 wherein the propellant means comprises a propellant charge.

42. A multipathway automatic and on-demand drug delivery system for multiple administrations at selectable dispensing times of at least one type of drug, said system comprising:

a plurality of drug storage and delivery means wherein each has at least one drug storage reservoir and an actuable drug delivery system which receives a signal causing the drug delivery system to eject the at least one type of drug from the at least one drug storage reservoir, said plurality of drug storage and delivery means comprising:

a first chamber for holding a first drug, wherein the first chamber is compressible to thereby eject a mixed drug from an ejection end thereof;

a second chamber for holding a second drug, wherein the second chamber is compressible to thereby eject the second drug therefrom;

a one-way port coupling the first chamber and the second chamber, whereby the second drug is introduced into the first chamber for mixing with the first drug to produce the mixed drug;

a first propellant charge for compressing the second chamber to force the second drug into the first chamber via the one-way port; and a second propellant charge for compressing the first chamber to thereby eject the mixed drug therefrom via the ejection ends a drug storage and delivery module which holds the plurality of drug storage and delivery means in position until ejection of the at least one type of drug therefrom;

a securing means for coupling the drug storage and delivery module to a patient; and a control means which is coupled to the drug storage and delivery module and which transmits the signal causing the drug delivery system to eject the at least one type of drug at the selectable dispensing times.

* * * * *